(12) United States Patent
Wang

(10) Patent No.: US 6,509,746 B1
(45) Date of Patent: Jan. 21, 2003

(54) EXCITATION CIRCUIT FOR COMPENSATED CAPACITOR INDUSTRIAL PROCESS CONTROL TRANSMITTERS

(75) Inventor: Rongtai Wang, Edina, MN (US)

(73) Assignee: Rosemount Inc., Eden Prairie, MN (US)

( * ) Notice: Subject to any disclaimer, the term of this patent is extended or adjusted under 35 U.S.C. 154(b) by 0 days.

(21) Appl. No.: 09/873,668

(22) Filed: Jun. 4, 2001

(51) Int. Cl.[7] .............................................. G01R 27/26
(52) U.S. Cl. .................................. 324/678; 340/870.37
(58) Field of Search ............................... 324/60, 60 C, 324/60 R, 678–679, 607, 706, 711; 341/143, 155; 73/718, 724, 780; 340/870.37

(56) References Cited

U.S. PATENT DOCUMENTS

| | | | |
|---|---|---|---|
| 3,657,653 A | * 4/1972 | Wilkinson | 325/38 B |
| 4,791,352 A | 12/1988 | Frick et al. | 324/60 |
| 4,878,012 A | 10/1989 | Schulte et al. | 324/60 |
| 5,083,091 A | 1/1992 | Frick et al. | 324/678 |
| 5,119,033 A | 6/1992 | Frick et al. | 324/607 |
| 5,329,818 A | 7/1994 | Frick et al. | 73/708 |
| 6,005,500 A | 12/1999 | Gahoury et al. | 341/43 |
| 6,140,952 A | * 10/2000 | Gaboury | 341/143 |
| 6,295,875 B1 | * 10/2001 | Frick et al. | 73/718 |

* cited by examiner

Primary Examiner—N. Le
Assistant Examiner—Amy He
(74) Attorney, Agent, or Firm—Westman, Champlin & Kelly, P.A.

(57) ABSTRACT

An industrial process control transmitter has a capacitive sensor having at least three outputs each responsive in differing amounts to a process condition and to sensor hysteresis. An excitation circuit charges the sensor and pumps the charges to a sigma-delta capacitance-to-digital converter. The excitation circuit includes a charge amplifier coupling one of the sensor outputs to a summing node for summing with a charge on at least one other output. An auto-zeroing switch re-sets the charge amplifier on each cycle of operation of the charge amplifier.

20 Claims, 8 Drawing Sheets

EXCITATION CIRCUIT FOR COMPENSATED CAPACITOR INDUSTRIAL PROCESS CONTROL TRANSMITTERS

FIELD OF THE INVENTION

The present invention is related generally to industrial process control transmitters, and particularly to a sensor excitation circuit for use in such transmitters.

BACKGROUND OF THE INVENTION

Industrial process control transmitters are used to measure process variables in field locations and provide standardized transmission signals as a function of the measured variable. The term "process variable" refers to a physical or chemical state of matter or conversion of energy, such as pressure, temperature, flow, conductivity, pH, and other properties. Process control transmitters are often operated in hazardous field environments to measure these variables and are connected by two-wire communication lines to a central or control station.

One such transmitter is described in U.S. application Ser. No. 09/312,411 filed May 14, 1999, now U.S. Pat. No. 6,295,875 granted Oct. 2, 2001, by Roger L. Frick and David A. Broden for "Pressure Sensor for a Pressure Transmitter", and assigned to the same assignee as the present invention. The Frick et al. transmitter employs a capacitive sensor having a deflectable sensing diaphragm and three or more capacitor electrodes forming separate capacitors with the diaphragm. Two of the capacitors are primary sensing capacitors that are arranged differentially so that the capacitances of the primary sensing capacitors change oppositely in proportion to the process variable. The third (and fourth, if used) capacitor is a compensation capacitor that provides signals representing certain offset errors, or hysteresis, associated with one or both of the primary capacitors.

The Frick et al. transmitter includes a sigma-delta converter that acts as a capacitance-to-digital converter. An excitation circuit provides a charge packet to the capacitors of the sensor, which are charged by an amount based on the capacitance value of the capacitor. The charge is transferred to an integrator/amplifier of the sigma-delta converter to derive a signal representative of sensor capacitance. The signal is processed and a standardized transmission signal is transmitted to the central control station via the two-wire communication lines.

The excitation circuit of the Frick et al. application includes separate, external operational amplifiers that invert the representations of the charges on the compensation capacitors and apply a gain adjustment to the charge. The separate operational amplifiers in the excitation circuit limit sampling frequency, introduce noise and consume precious power. Additionally, current operational amplifiers require substantial portions of the sample cycle for the output voltage to settle (slew). The consumption of current during this long settling time, results in insufficient current being available for other purpose, such as for diagnostics.

SUMMARY OF THE INVENTION

The present invention is directed to an industrial process control transmitter that employs integrated inverting amplifiers that require less current to settle the output signal. Consequently, more current is available for diagnostic and other purposes. Additionally, an auto-zeroing switch reconfigures the integrated inverting amplifiers to unity gain amplifiers so that less current is required for settling the output voltage and more current is available for diagnostic and other purposes.

The industrial process control transmitter has a capacitive sensor adapted to monitor a process condition. The sensor has at least two primary sensing capacitors that respond oppositely to the process condition, and at least a third compensation capacitor that responds to error or hysteresis in a manner differently from either primary sensing capacitor. A sensing circuit includes a charge summing node, an integrated inverting charge amplifier coupling the compensation capacitor to the summing node, and a sigma-delta capacitance-to-digital converter circuit coupled to the summing node providing a digital output representative of the process condition. A transmitter output circuit receives the digital output and generates a standardized transmitter output adapted for coupling to a remote receiver.

The capacitors are charged by a charge circuit that operates in phases such that a sensing capacitor is charged during one phase and its charge is transferred to the sigma-delta circuit during a second phase. In preferred embodiments the second phase has a longer time duration than the first phase, so the output of the inverting amplifier has more time to settle and the amplifier requires less current than prior amplifiers.

In another embodiment, the integrated inverting amplifier is shared by two compensation capacitors operated during different sensing cycles.

DETAILED DESCRIPTION OF THE PREFERRED EMBODIMENTS

Figure 6:
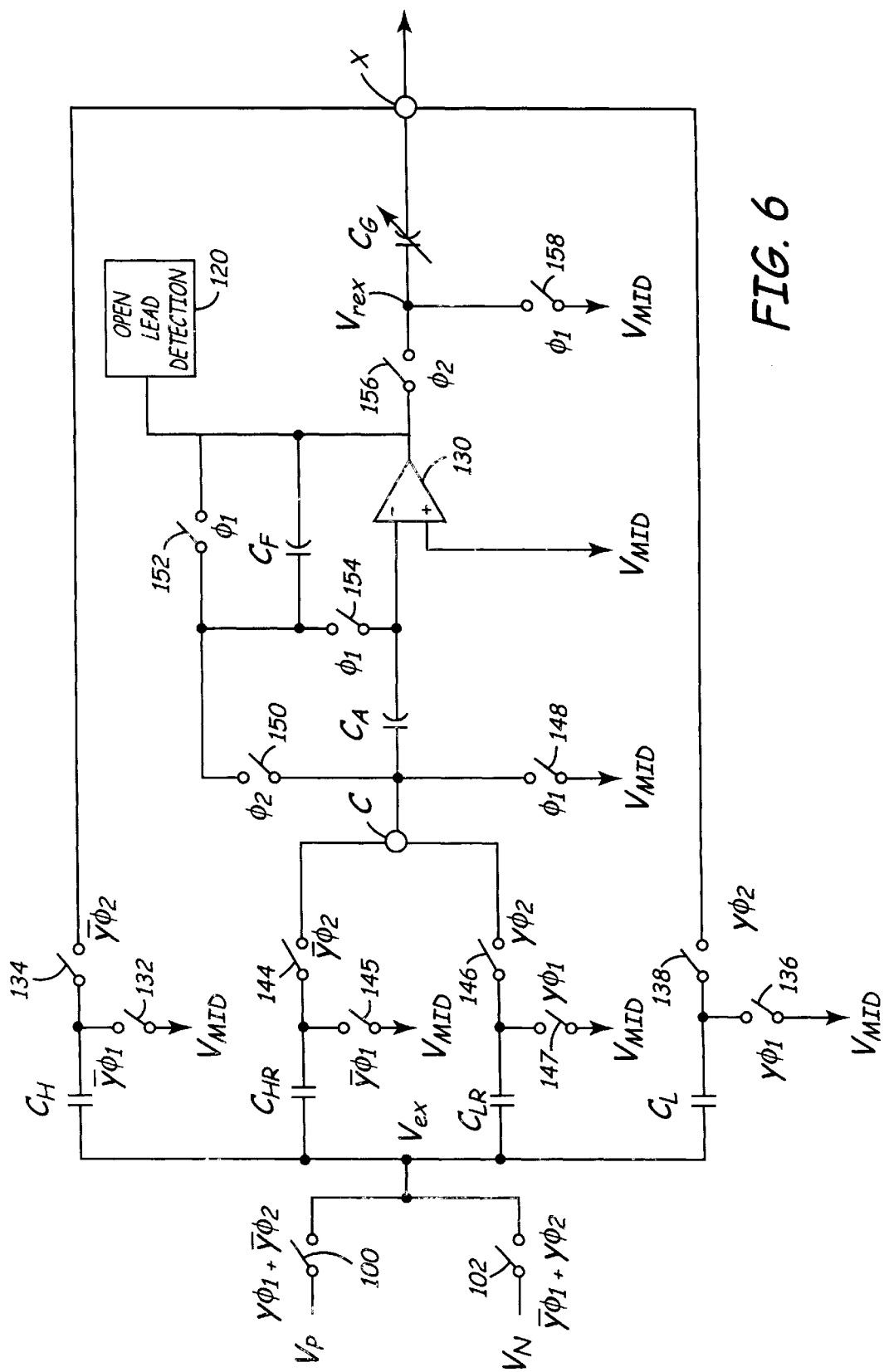
FIG. 6 is a circuit diagram of an excitation circuit according to a third embodiment of the present invention.

The principal problem addressed by the present invention is that the prior amplifiers that inverted the charges from the compensation capacitors required considerable power. The power requirements of prior inverting amplifiers adversely affected performance, and left no power for other purposes, such as for diagnostic circuits. The present invention employs an auto-zeroing switch that reduces the current required for the output, and hence reduces the power requirements of the inverting amplifiers. The embodiment of FIG. 6 provides additional power reduction by sharing a single inverting amplifier between two compensation capacitors.

Figure 1:
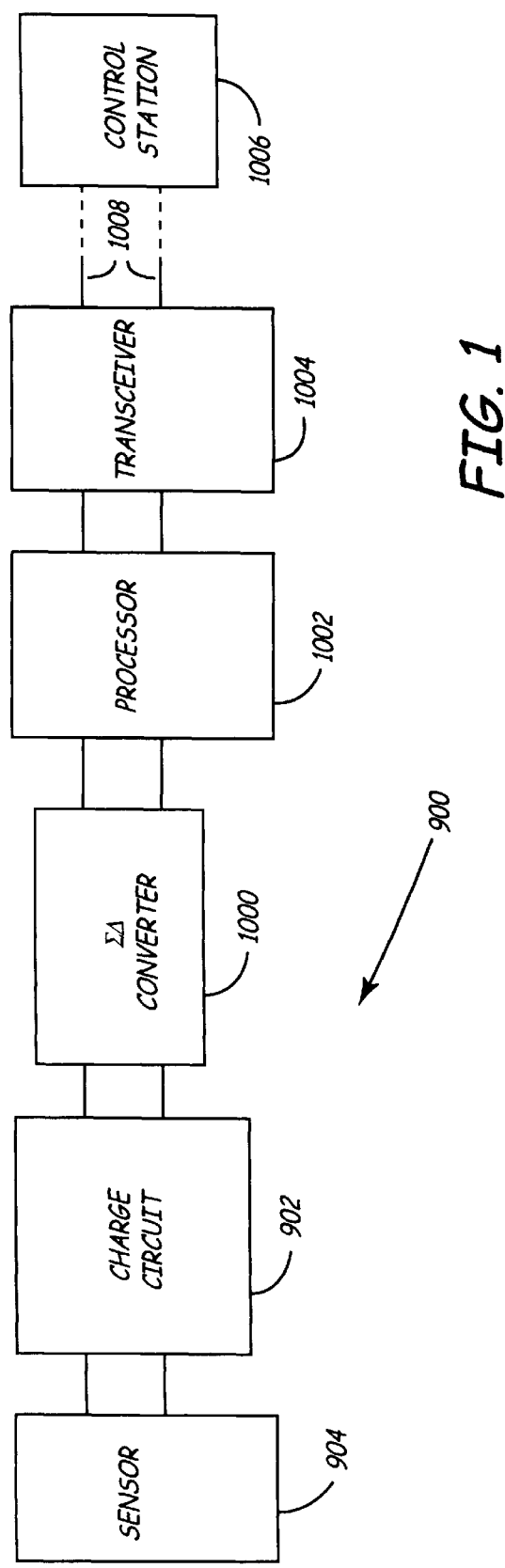
FIG. 1 is a block diagram of an industrial process control transmitter employing a sensor excitation circuit according to the present invention.

FIG. 1 is a block diagram of an industrial process control transmitter 900 having a sigma-delta circuit 1000 arranged to receive signals representative of a pressure from charge circuit 902 that charges pressure sensitive capacitors of sensor 904. Charges on the capacitors are representative of pressure, and of sensor hysteresis, and are transferred to circuit 1000 by charge circuit 902. Circuit 1000 converts the charges to digital signals which are processed by processor 1002 and input to transceiver 1004 which provides a standardized transmission signal in a protocol designed for transmission to central control station 1006 by a two-wire communication link 1008. Additionally, control station 1006 may send signals to remote industrial process control transmitter 900 by communication link 1008 which are received through transceiver 1004 to provide control to transmitter 900 in a manner well known in the art.

Figure 2:
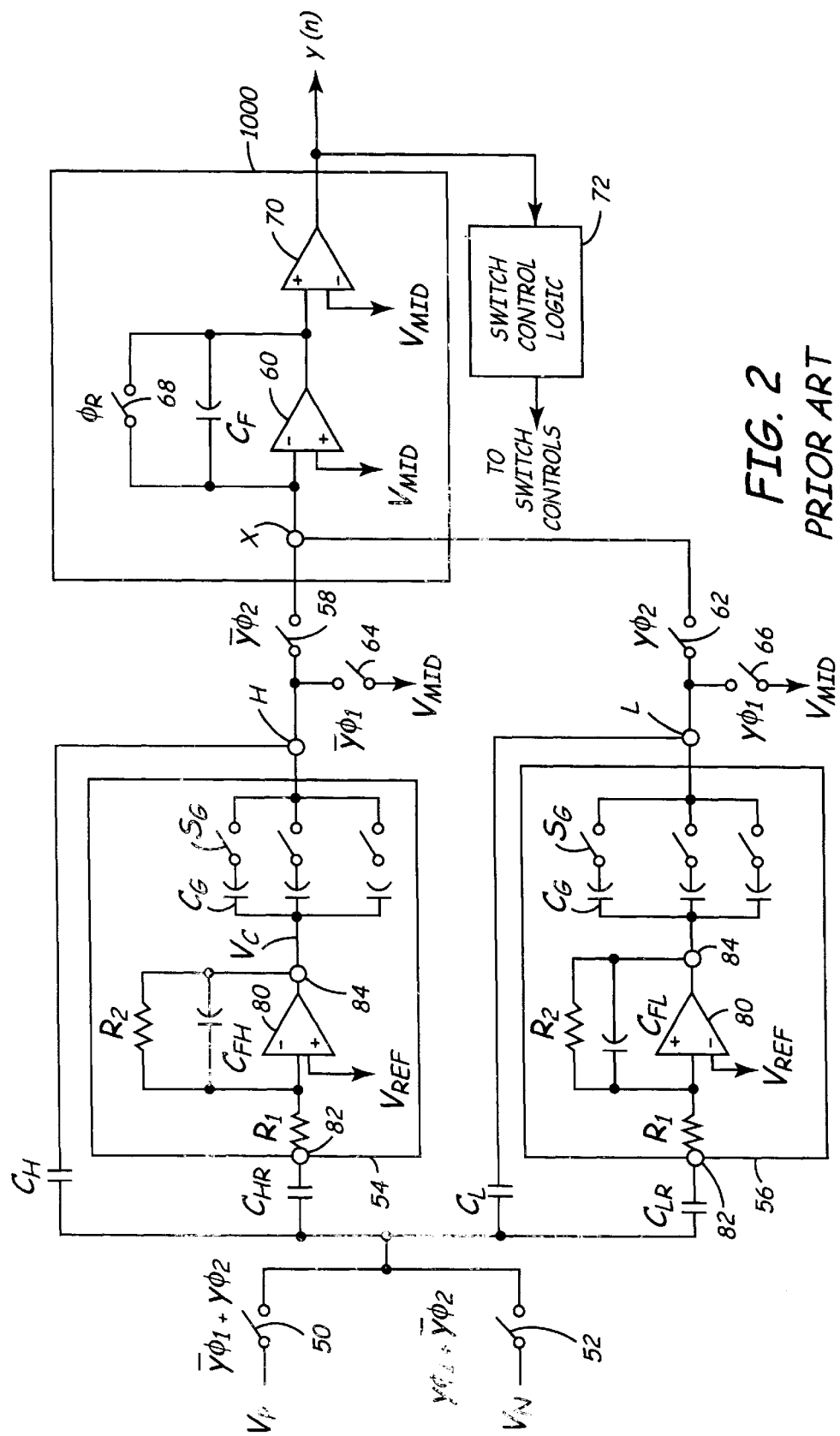
FIG. 2 is a circuit diagram illustrating the excitation and sigma-delta compensation circuit described in the Frick et al. application.

FIG. 2 is a circuit diagram illustrating the excitation circuit and sigma-delta circuit 1000 of an industrial process control transmitter described in the Frick et al. application. The capacitive sensor is schematically represented as primary capacitors $C_H$ and $C_L$ and compensation capacitors $C_{HR}$ and $C_{LR}$. As described in the Frick et al. application, the sensor physically changes over time causing errors, known as hysteresis. These errors are a common source of error in measuring the process variable condition by the industrial process control transmitter. The compensation capacitors $C_{HR}$ and $C_{LR}$ have a proportionately greater response to sensor hysteresis than the primary capacitors $C_H$ and $C_L$.

An input side of each capacitor $C_H$, $C_L$, $C_{HR}$ and $C_{LR}$ is coupled through switches 50 and 52 to the respective supplies $V_P$ and $V_N$. The output sides of capacitors $C_{HR}$ and $C_{LR}$ are connected to respective inverter charge amplifiers circuits 54 and 56, the outputs of which are connected to the output of the respective capacitor $C_H$ and $C_L$ at nodes H and L, respectively. Nodes H and L are connected through respective switches 58 and 62 to node X at the negative input of amplifier 60, and through respective switches 64 and 66 to voltage source Vmid.

Amplifier 60 is an integrating amplifier that operates as an integrator amplifier for the first, or modulator, stage of sigma-delta capacitance-to-digital converter 1000. Amplifier 60 provides an increasing negative output for an increasing positive signal input at the negative input, and providing an increasing positive output for an increasing negative signal input at the negative input. A reset switch 68 is connected in parallel to capacitor $C_F$ to reset the circuit. The output of amplifier 60 is connected to the positive input of amplifier 70, whose output provides a digital output representing the capacitance ratio. Amplifier 70 serves as the differential amplifier of the second, or controller, stage of sigma-delta circuit 1000. Sigma-delta circuit 1000, also known as a delta-sigma, $\Sigma\Delta$, or $\Delta\Sigma$ circuit, is an analog-to-digital converter that generates an alternating polarity balanced current to an integrator under control of a clocked controller. The output of amplifier 70 is also connected to switch control logic 72 to control operation of the switches.

Figure 3:
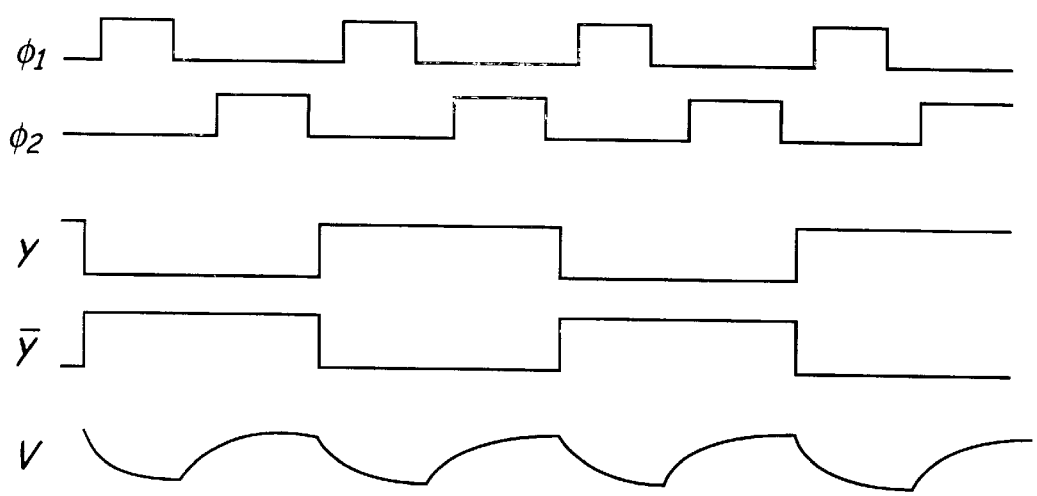
FIG. 3 is a timing diagram for the circuits illustrated in FIGS. 2, 4 and 5.

Switch control logic 72 provides four switch logic signals $\Phi_1$, $\Phi_2$, y and $\bar{y}$ (y-not), illustrated in FIG. 3. Signals $\Phi_1$ and $\Phi_2$ are non-overlapping phase signals, whereas signals y and $\bar{y}$ are complementary signals representing whether the circuit is operating in the positive or negative mode at a particular time. When operating in a positive mode, $\bar{y}$ is high, whereas when operating in a negative mode, y is high.

In the positive mode of the circuit ($\bar{y}$ high), switches 50 and 64 conduct during a first phase ($\Phi_1$) so the input sides of capacitors $C_H$ and $C_{HR}$ are at the positive voltage $V_P$ of the voltage supply. The output side of capacitor $C_H$ is at Vmid, which may be electrical ground, and the output side of capacitor $C_{HR}$ is at a voltage between $V_P$ and Vmid based on compensation capacitor(s) $C_G$.

While $\bar{y}$ is still high, during the second $\Phi_2$ phase, switches 52 and 58 conduct and 50 and 64 are non-conducting. With $V_N$ at the input of capacitor $C_H$, a negative charge representative of the capacitance value of capacitor $C_H$ is transferred to node H; with $V_N$ at the input of capacitor $C_{HR}$, a negative charge representative of the capacitance value of capacitor $C_{HR}$ is transferred to the negative input of inverter amplifier 80 of charge amplifier circuit 54. Capacitor(s) $C_G$ adjust the gain of amplifier 80 to set a constant $K_H$ based on the ratio of $C_G/C_{FH}$ for charge amplifier 54. Hence, the output of amplifier circuit 54 represents an adjusted inverted charge, $-K_H C_{HR}$, where $K_H$ is derived from the capacitor array $C_G$. The representation of $-K_H C_{HR}$ is summed with the representation of the charge on capacitor $C_H$ at node H. Switch 58 transfers the negative charge representation of $C_H - K_H C_{HR}$ from node H to node X at the negative input of amplifier 60. Amplifier 60 integrates the signal such that the negative input produces a positive change to the signal at the output of amplifier 60.

The circuit associated with capacitor $C_L$ and $C_{LR}$ operates in a similar manner during the phases while y is high to place a positive charge at the negative input of amplifier 60, thereby stepping the output of amplifier 60 negatively.

The circuit is reset by operating switch 68 during a reset phase $\Phi_R$ to discharge feedback capacitor $C_F$. Resistor $R_2$ has a high resistance (e.g., 100 megaohms) in parallel with feedback capacitor $C_{FN}$ to discharge capacitor $C_{FN}$ over the RC time constant of resistor $R_2$ and capacitor $C_{FN}$. The resistance of resistor $R_2$ must be large enough to minimally affect the transfer of charge to the integrator, yet small enough to effectively discharge capacitor $C_{FN}$ during resetting of the circuit. In practice, resistor $R_2$ was chosen high enough as to minimally impact the integration of the charge signal, and require resetting of the circuit over a considerably longer time period.

One problem associated with the circuit illustrated in FIG. 2 is that operational amplifiers 80 have an input resistance $R_1$ of about 5,000 ohms. The input resistance of amplifiers 80, coupled with the small current available to the amplifiers to settle the output voltage, introduces delays in integrator settling. These delays are illustrated at waveform Vc in FIG. 3 which illustrates the slow settling of the output of amplifier 80. More particularly, the long settling times between triggering a change in the Vc voltage and settling to the new voltage level resulted in shortened periods of settled Vc voltage, resulting in reduced current available for other purposes. The slow integrator settling creates measurement error at high sampling frequencies and deprives the circuit of adequate power to operate other diagnostic circuits. Moreover, the distorted waveform output $V_C$ may adversely affect the integrator settling of the first stage integrator 60 of sigma-delta converter 1000.

Another problem with the circuit illustrated in FIG. 2 is that amplifiers 80 were implemented as external amplifiers, connected by terminal 82 to the respective compensation capacitor $C_{HR}$ or $C_{LR}$, and by terminal 84 to gain capacitor array $C_G$. The connections to external amplifiers 80 introduced additional leakage paths and noise sources for the circuit.

Another problem of the circuit of FIG. 2 was that operational amplifiers 80 required the addition of two sample-and-hold amplifiers within amplifier 60 which added to the power consumption of the circuit, and diminished real estate (chip area) availability on the circuit boards.

Figure 4:
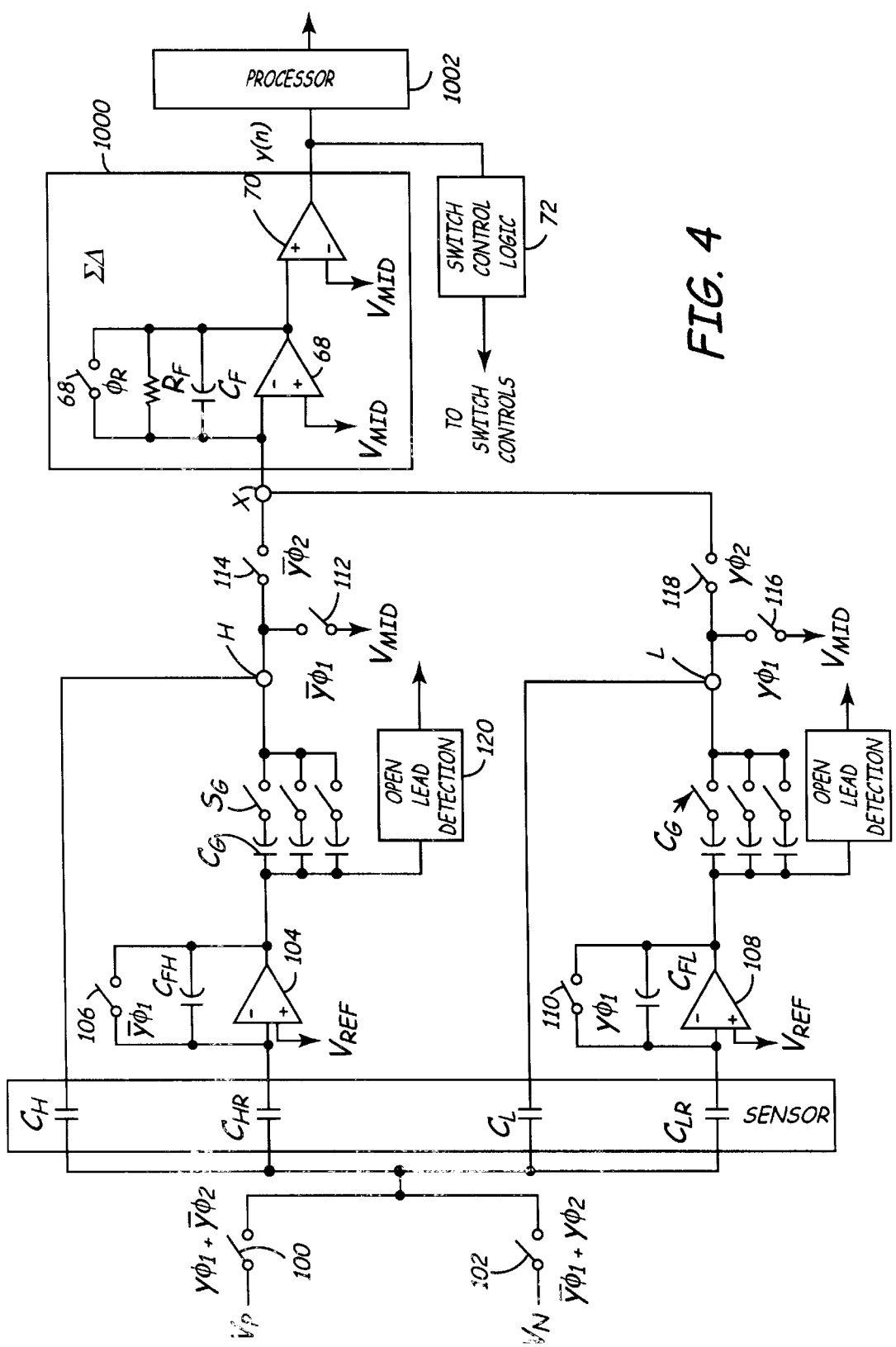
FIG. 4 is a circuit diagram of an excitation circuit according to a first embodiment of the present invention.

FIG. 4 is a circuit diagram of the excitation circuit in accordance with the first embodiment of the present invention coupled to the sigma-delta capacitive-to-digital circuit and digital processor of an industrial process control transmitter. A power supply supplies positive and negative voltage levels $V_P$ and $V_N$ through respective switches 100 and 102 to the common side of the sensor capacitors $C_H$ and $C_L$ and the compensation capacitors $C_{HR}$ and $C_{LR}$ of the sensor. The output side of sensor capacitor $C_H$ is connected to node H, and the output side of sensor capacitor $C_L$ is connected to node L. The output side of compensation capacitor $C_{HR}$ is connected to the negative input of on-chip amplifier 104 whose positive input is connected to a reference voltage level Vref of the power supply, and whose output is connected to programmable gain capacitor array $C_G$ having program switches $S_G$. The output of capacitor array $C_G$ is connected to node H. Feedback capacitor $C_{FH}$ is connected between the output and negative input of amplifier 104. Auto-zeroing switch 106 is connected across capacitor $C_{FH}$.

Similarly, the output of compensation capacitor $C_{LR}$ is connected to the negative input of on-chip amplifier 108 whose positive input is connected to the reference voltage level Vref and whose output is connected to programmable gain capacitor array $C_G$ to the output node L. Feedback capacitor $C_{FL}$ is connected between the negative input and output sides of amplifier 108, and auto-zeroing switch 110 is connected across capacitor $C_L$.

Voltage level Vmid of the power supply is connected to node H by switch 112. Similarly, voltage level Vmid is connected to node L by switch 116. Node X, which is the input node to sigma-delta circuit 1000, is connected to node H by switch 114 and to node L by switch 118.

Node X is coupled to the input of integrating amplifier 60 of the first stage of sigma-delta circuit 1000. The output of sigma-delta circuit 1000 is connected to switch control logic 72 to operate the switches of the excitation circuit and to digital processor 1002. Processor 1002 derives a standardized signal for transmission via a two-wire communication system 1004 to a central receiving station (not shown). Examples of communication system 1004 include a 4–20 milliAmpere (mA) communication system, a FieldBus system, or a fiber optic system, commercially available from Rosemount Inc. of Eden Prairie, Minn., and may operate in various protocols including frequency modulation, amplitude modulation and phase modulation.

In operation of the circuit illustrated in FIG. 4, and with reference to the waveforms illustrated in FIG. 3, during a first cycle of the operation signal $\overline{y}$ is high. During the first phase $\Phi_1$, switches 102, 106 and 112 conduct, and switches 100 and 114 are non-conductive. Sensing capacitor $C_H$ is charged by the voltage $V_N$ to create a voltage across capacitor $C_H$ representative of Vmid-$V_N$.

Conduction of auto-zeroing switch 106 configures amplifier 104 to a unity-gain amplifier whose output is equal to Vref (ignoring any voltage offset of the amplifier). The presence of Vref on the output side of capacitor $C_{HR}$ and the presence of $V_N$ on the input side creates a voltage across capacitor $C_{HR}$ representative of Vref-$V_N$.

During the next phase, $\Phi_2$, switches 100 and 114 conduct and switches 102, 106 and 112 are non-conducting, placing a positive voltage $V_P$ on the input or common plate of capacitor $C_H$ and $C_{HR}$, and connecting node H to node X. The change of voltage on the input side of sensing capacitor $C_H$ from $V_N$ to $V_P$ causes capacitor $C_H$ to pump a positive charge to node H. The charge pumped by capacitor $C_H$ is representative of the capacitance of capacitor $C_H$ and voltage $V_N$. At the same time, the voltage on the input side of capacitor $C_{HR}$ rises from $V_N$ to $V_P$, causing capacitor $C_{HR}$ to pump a positive charge into feedback capacitor $C_{FH}$. The charge pumped by capacitor $C_{HR}$ is representative of the capacitance of capacitor $C_{HR}$ and the voltage Vref-$V_N$. Amplifier 104 inverts the charge from capacitor $C_{HR}$, creating a negative voltage increment at its output. The negative voltage increment is gain adjusted by gain capacitor array $C_G$ producing a negative increment output proportional to $C_{HR}(C_G/C_{FH})$, where the ratio $C_G/C_{FH}$ is the gain of the capacitor charge circuit. Hence, the gain of capacitor array $C_G$ represents a programmed gain value. The gain adjusted compensation charge is also based on the reference voltage Vref, which may be equal to, or different from, Vmid. The gain ratio $C_G/C_{FH}$ and reference voltage value are established at manufacture based on performance of the sensor, and may be re-set in the field by adjusting switches $S_G$ and/or resetting the power supply.

The positive charge output of sensing capacitor $C_H$ is combined with the gain-adjusted negative charge output from compensation capacitor $C_{HR}$ at node H and are transferred during the second cycle, $\Phi_2$, to node X for input to the sigma-delta converter.

The low side of the circuit illustrated in FIG. 4 operates in a similar manner except that in this case auto-zeroing occurs when switch 100 is conducting and the charge compensation occurs during the conductive condition of switch 102.

Because the voltage output of amplifier 104 is proportional to the reference voltage, the amplifier may be designed so that adequate current is available to drive other circuitry. More particularly, the reference voltage may be adjusted independently of the level of Vmid to provide adequate current for amplifier 104, 108. Thus, FIG. 4 illustrates an open lead detection circuit 120 connected to the output of amplifier 104 to detect an open circuit condition in the compensation capacitor circuit. For example, a compensation capacitance $C_{HR}$ having normal operation between about 20 and 80 picofarads (pf) produces a voltage increment from amplifier 104 between about 0.5V and 2.0V. If the connection to capacitor $C_{HR}$ becomes open-circuited, the capacitance would drop to below about 6 pf, dropping the corresponding voltage output of amplifier 104 to below about 0.15V. Consequently, a simple comparator circuit may be used to detect an open lead condition. Other diagnostic circuits may also be driven by amplifiers 104 and 108, depending on current availability.

Figure 5:
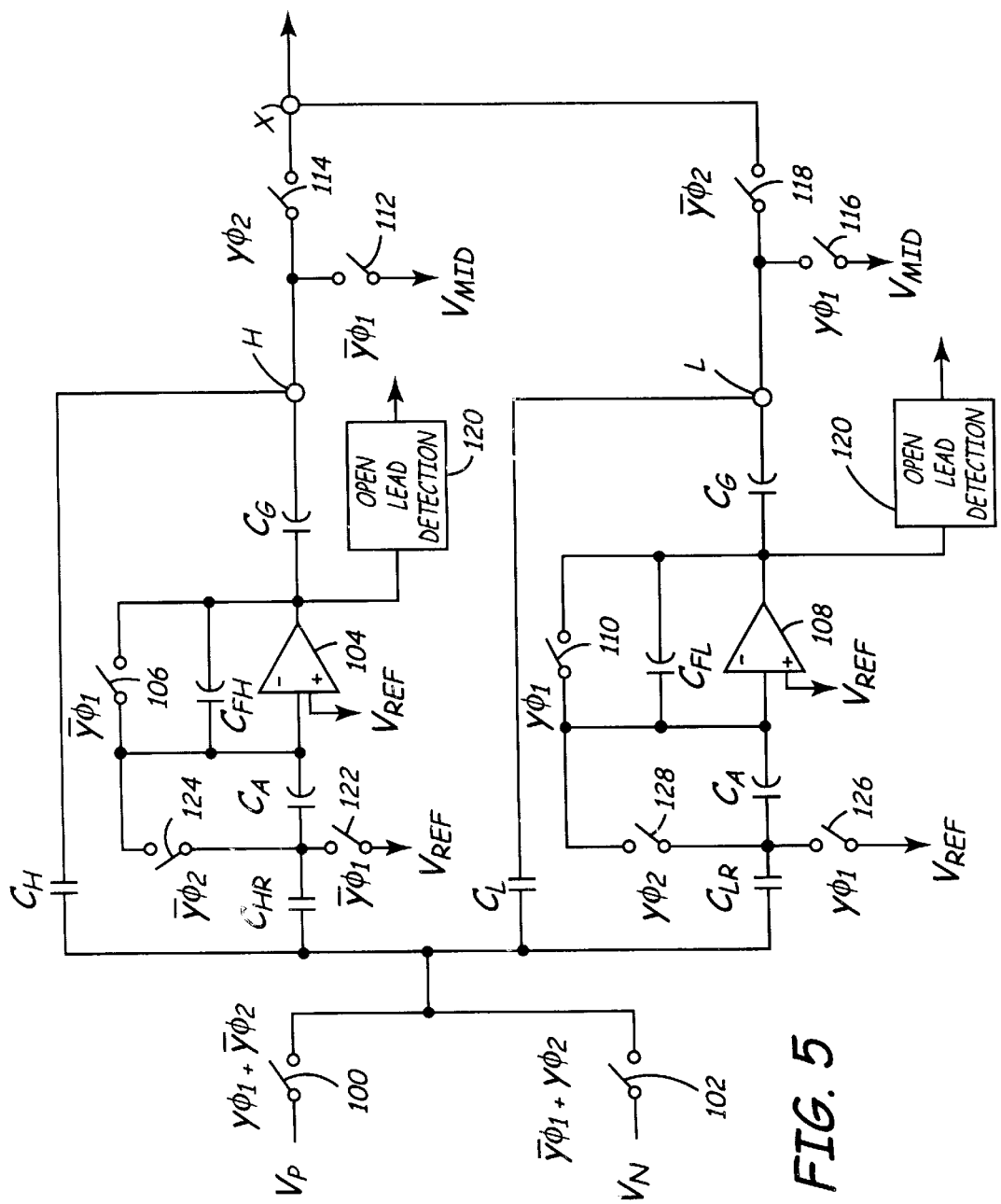
FIG. 5 is a circuit diagram of an excitation circuit according to a second embodiment of the present invention.

FIG. 5 illustrates a second embodiment of an excitation circuit in accordance with the present invention. The principal difference between the circuit illustrated in FIG. 5 and that illustrated in FIG. 4 resides in the inclusion of offset capacitor $C_A$ which stores any voltage offset in the compensation amplifier. Thus, as illustrated in FIG. 5, capacitor $C_A$ is coupled between the compensation capacitor and the negative input of the respective integrating amplifier.

Differential amplifiers, such as amplifiers 104 and 108, are designed to provide a balanced output upon receipt of a balanced input. For example, if the positive and negative inputs to the amplifier are equal and opposite (e.g., the positive input receiving +5V while the negative input receives −5V), the amplifier should produce a zero output. In practice, however, the amplifier may not be absolutely balanced. Even with balanced inputs, the amplifier might produce a slightly offset output voltage. While offset is not always a problem, in some cases it might be desirable to correct this offset. One correction technique comprises an offset capacitor $C_A$ that stores a value representative of amplifier offset and combines that value with one of the amplifier inputs to adjust the amplifier for offset. Hence, the circuit of FIG. 5 employs an offset capacitors $C_A$ coupled between capacitor $C_{HR}$ and the negative input of amplifier 104 and between capacitor $C_{LR}$ and the negative input of amplifier 108.

Switch 122 is coupled between voltage level Vref of the power supply and the output of compensation capacitor $C_{HR}$, and switch 124 is coupled between the output of capacitor $C_{HR}$ and feedback capacitor $C_{FH}$. Similarly, switch 126 is coupled between the output of compensation capacitor $C_{LR}$ and voltage level Vref, and switch 128 is coupled between the output of capacitor $C_{LR}$ and feedback capacitor $C_{FL}$.

The circuit illustrated in FIG. 5 operates in a manner similar to the circuit illustrated in FIG. 4, except that when signal $\Phi_1$ is high switch 122 or 126 provides the Vref voltage level to charge respective compensation capacitor. Thus, capacitor $C_{HR}$ is charged to produce a positive charge at its output by virtue of the voltage difference between voltage levels $V_N$ and Vref during the $\bar{y}$ cycle. Auto-zeroing switch 106 short circuits feedback capacitor $C_{FH}$ so that the offset voltage of amplifier 104 is stored in capacitor $C_A$. During the second phase when $\Phi_2$ is high, switches 106 and 122 are non-conducting and the charge of capacitor $C_{HR}$ is transferred through conducting switch 124 to the feedback capacitor $C_{FH}$ to provide a positive charge to node H. The charge at node H is based on the ratio $C_G/C_{FH}$, as previously described. During the $\Phi_1$ phase, a charge is generated on capacitor $C_H$ providing a positive charge to node H. The negative charge from sensing capacitor $C_H$ is summed with the positive charge derived from compensation capacitor $C_{HR}$ for delivery to node X and sigma-delta compensator.

FIG. 6 illustrates a third embodiment of an excitation circuit in accordance with the present invention. The circuit illustrated in FIG. 6 is similar to that of FIG. 5, except that a single amplifier 130 and gain capacitor array is employed. Thus, as illustrated in FIG. 6, the common plate or terminal of capacitors $C_H$, $C_{HR}$, $C_L$ and $C_{LR}$ is connected to voltage source $V_P$ or $V_N$ through switches 100 and 102, respectively. The output side of capacitor $C_H$ is connected through switch 132 to voltage level Vmid and is connected through switch 134 to node X. Similarly, the output side of capacitor $C_L$ is connected through switch 136 to voltage source Vmid and through switch 138 to node X. The output side of compensation capacitor $C_{HR}$ is connected through switch 144 to node C and through switch 145 to voltage level Vmid. Similarly, the output side of compensation capacitor $C_{LR}$ is connected through switch 146 to node C and through switch 147 to voltage level Vmid. Switch 148 selectively connects node C to voltage level Vmid, and switch 150 selectively connects node C to one side of feedback capacitor $C_F$. Offset capacitor $C_A$ is coupled between node C and the negative input of amplifier 130. Auto-zeroing switch 152 is connected in parallel with feedback capacitor $C_F$, and switch 154 is coupled between feedback capacitor $C_F$ and the negative input of amplifier 130. The positive input of amplifier 130 is connected directly to voltage level Vmid.

The output of amplifier 130 is connected through switch 156 to the input of gain capacitor array $C_G$, whose output is connected to node X. The input of capacitor array $C_G$ is also connected through switch 158 to voltage level Vmid.

Operation of the circuit illustrated in FIG. 6 may best be explained with reference to the waveforms illustrated in FIG. 7. Voltage Vex at the common plate of capacitors $C_H$, $C_{HR}$, $C_L$ and $C_{LR}$ varies between high and low voltages centered about a midpoint voltage, Vmid. In the preferred form of the embodiment of FIG. 6, Vex is a pulse waveform that vary between +1.25 volts and +3.75 volts around a midpoint voltage level, Vmid (+2.5 volts). Moreover, the difference ($\Delta$Vex) between the high and low values of Vex is preferably equal to Vmid.

Considering the side of the circuit associated with sensing capacitor $V_H$ and $V_{HR}$, during the y cycle signal Vex is high (+3.75V) during the first phase ($\Phi_1$) and is low (+1.25V) during the second phase ($\Phi_2$). During the auto-zeroing phase ($\Phi_1$), switches 145, 148, 152, 154 and 158 are conducting. Switch 145 couples the output side of capacitor $C_{HR}$ to voltage level Vmid, thereby charging the capacitor to +1.25V (high level of Vex minus Vmid). The conducting condition of switch 152 discharges feedback capacitor $C_F$, thereby resetting the voltage across capacitor $C_F$ to zero. The conducting condition of switches 148 and 154 stores the offset voltage of amplifier 130 in offset capacitor $C_A$. The conducting condition of switch 158 places the Vmid voltage level (+2.5V) at the input side of gain capacitor $C_G$.

During phase $\Phi_2$, switches 145, 148, 152, 154 and 158 are non-conducting, switches 144, 150 and 156 are conducting, and the voltage Vex drops to its low level (+1.25V). Compensation capacitor $C_{HR}$ is connected to node C. The lower voltage level of Vex forces the input level of capacitor $C_{HR}$ to drop, forcing the voltage at node C to drop to 0V. The 0V level at node C creates an excess charge at node C of $\Delta Q=-\Delta Vex \cdot C_{HR}$. This excess charge is transferred to feedback capacitor $C_F$ through switch 150. Amplifier 130 and feedback capacitor $C_F$ form an integrator to create a positive voltage step to voltage Vc at the output of amplifier 130. With switch 156 conducting and switch 158 non-conducting, the voltage Vrex at the input of gain capacitor $C_G$ is directly connected to voltage Vc, which settles at Vmid+$\Delta$Vex·$C_{HR}$/$C_F$. Therefore, Vrex, at the input of gain capacitor array $C_G$, varies between Vmid during phase $\Phi_1$ and Vmid+$\Delta$Vex·$C_{HR}$/$C_F$ during phase $\Phi_2$. During phase $\Phi_2$, gain capacitor array $C_G$ adjusts the gain of the Vrex voltage to charge node X by $$+\Delta Vex \frac{C_G \cdot C_{HR}}{C_F}.$$

The sensing capacitor $C_H$ is charged to +1.25 v during the first phase $\Phi_1$ due to the conducting condition of switch 132 placing Vmid (+2.5 v) on the output side of capacitor $C_H$ and the high positive input of Vex (+3.75 v) at the input side of the capacitor. During the second phase $\Phi_2$, the input voltage Vex drops to +1.25 v, placing a negative charge ($-\Delta$Vex·$C_H$) on the output side of capacitor $C_H$. This charge is transferred by switch 134 to node X, where it is summed with the charge, $$+\Delta Vex \frac{C_G \cdot C_{HR}}{C_F},$$

from the gain-adjusted compensation capacitor $C_{HR}$, resulting in a charge at node X of $$-\Delta Vex\left[C_H - \frac{C_G \cdot C_{HR}}{C_F}\right],$$

or, more simply, $-\Delta Vex(C_H - K \cdot C_{HR})$, where K is a constant equal to the ratio $C_G/C_F$. It will be appreciated that the constant K may be adjusted differently for the high and low sides of the sensor, simply by adjusting the gain codes for the capacitor array $C_G$. Gain capacitor array $C_G$ is shown as a variable capacitor of sake of simplicity, but it may be in the form illustrated in FIG. 4 employing a plurality of capacitors and switches that are operated under program. Consequently, the switches of the capacitor array may be operated differently during the y and $\overline{y}$ cycles simply by employing different program codes during the respective y and $\overline{y}$ cycles. Thus, the gain capacitance array may be set to one gain capacitance, $C_{GH}$, for the high side of the sensor and may be set to a different gain capacitance, $C_{GL}$, for the low side of the sensor, simply by using a different switch control logic during the two modes y and $\overline{y}$ of operation. For the high side, the charge at node X is $-\Delta Vex(C_H - K_H \cdot C_{HR})$, where $K_H$ is the ratio $C_{GH}/C_F$; for the low side, the charge at node X is $+\Delta Vex(C_L - K_L \cdot C_{LR})$, where $K_L$ is the ratio $C_{GL}/C_F$. Consequently, the charge pumped into node X is proportional to the respective one of $C_H - K_H \cdot C_{HR}$ or $C_L - K_L \cdot C_{LR}$.

Figure 7:
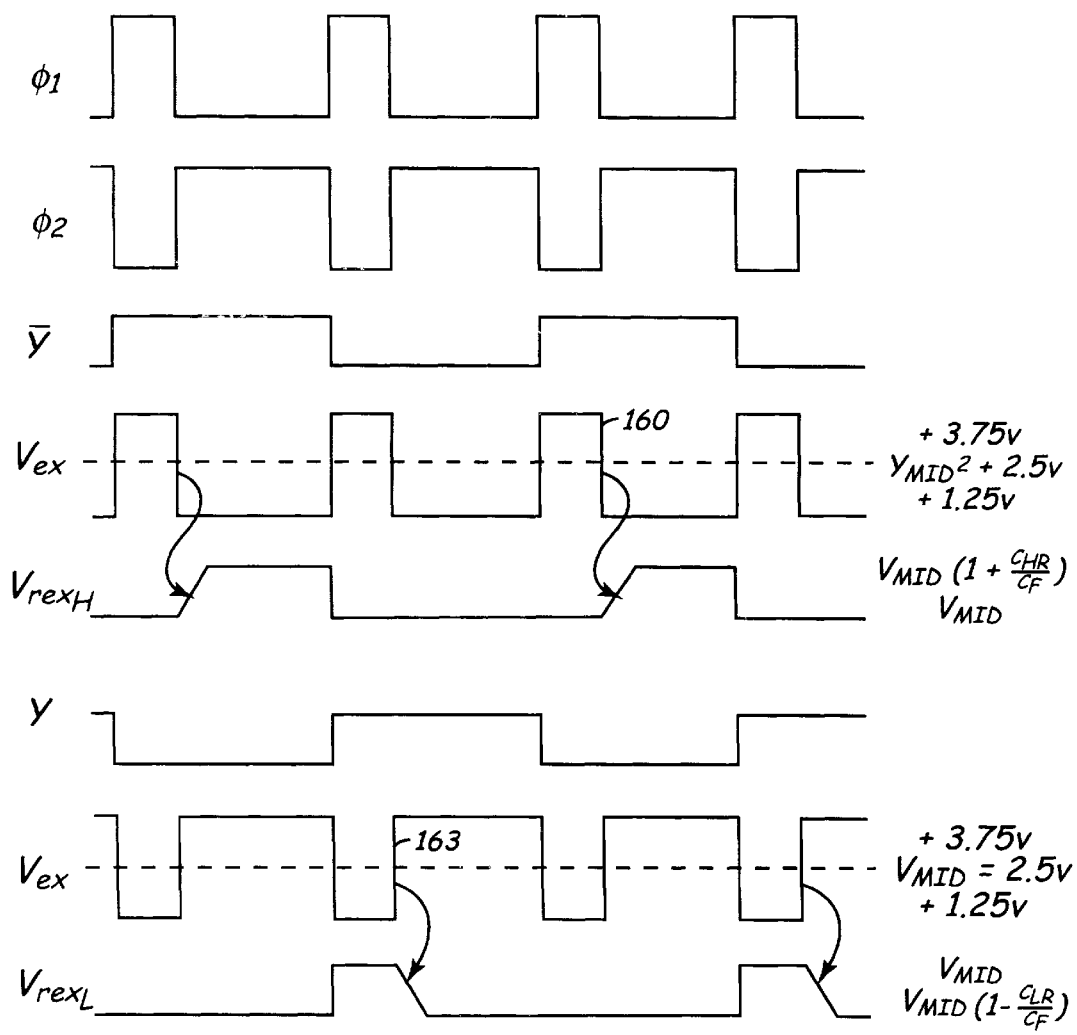
FIG. 7 is a timing diagram for the circuit illustrated in FIG. 6.

One feature of the invention is illustrated in FIG. 7. The rise time of the $Vrex_H$ pulse waveform and fall time of the $Vrex_L$ pulse waveform are not as sharp as that of the respective input signal Vex. Thus, the falling edge 160 of Vex forms the rising edge of $Vrex_H$ and the rising edge 163 of Vex forms the falling edge of $Vrex_L$. The rise or fall time of the Vrex signal is dependent on the current of amplifier 130; a large current is required to create a sharp edge to Vrex, and thereby reduce the period for Vrex to settle upon rise or fall (slew). Amplifier current of 260 microamperes ($\mu$A) and static current of 400 $\mu$A are required to transfer charges to the integrator of the sigma-delta converter from a 100 picofarad (pf) compensation capacitor during a 7.5 microsecond ($\mu$s) charge phase with a slew period of 1.5 $\mu$s. The embodiment of FIG. 6 employs a single inverting amplifier 130, resulting in a savings of about 400 $\mu$A current consumption. Moreover, as shown in FIG. 7, the durations of the $\Phi_1$ and $\Phi_2$ phases may be set unequal. In the preferred form of the invention, the $\Phi_1$ charge phase is reduced to 3.75 $\mu$s, whereas the $\Phi_2$ integration phase is increased to 11.25 $\mu$s (total duration of a cycle of operation is unchanged at 15 $\mu$s). This permits increasing the slew period to as much as 3.25 $\mu$s, which reduces current requirements to about 120 $\mu$A and amplifier static current to about 240 $\mu$A, thereby further reducing current consumption and improving settlement characteristics of the integrator. Moreover, the reduced current requirement allows current to be available for other functions, such as diagnostic circuits like open lead detector 120.

Figure 8:
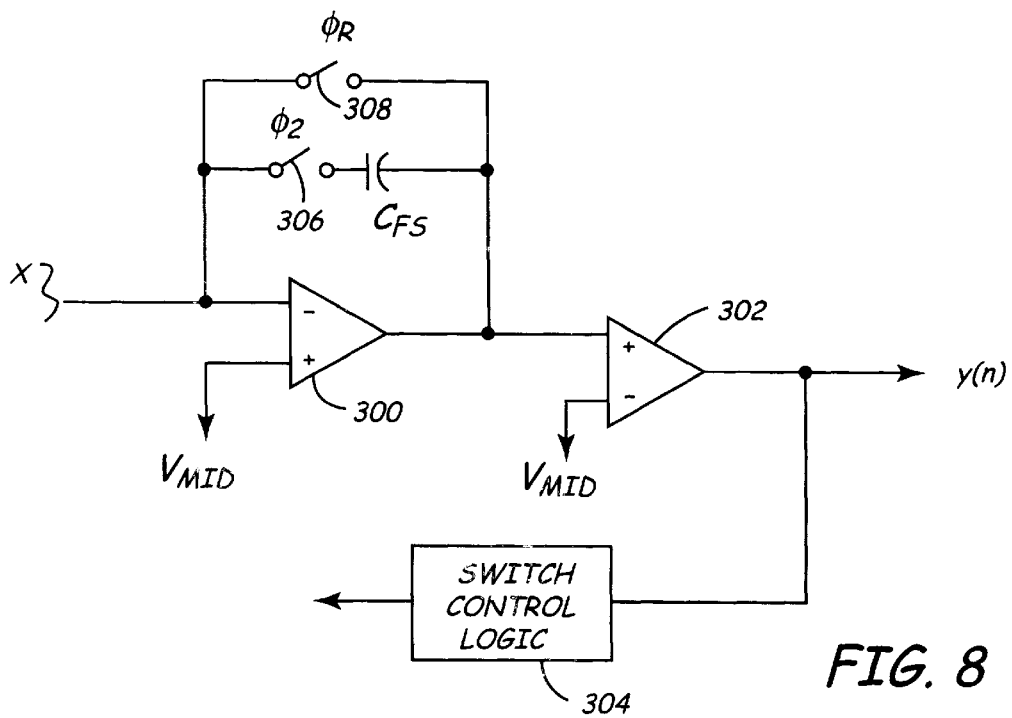
FIG. 8 is a circuit diagram of a first embodiment of a sigma-delta converter useful with the excitation circuit of the present invention.
Figure 9:
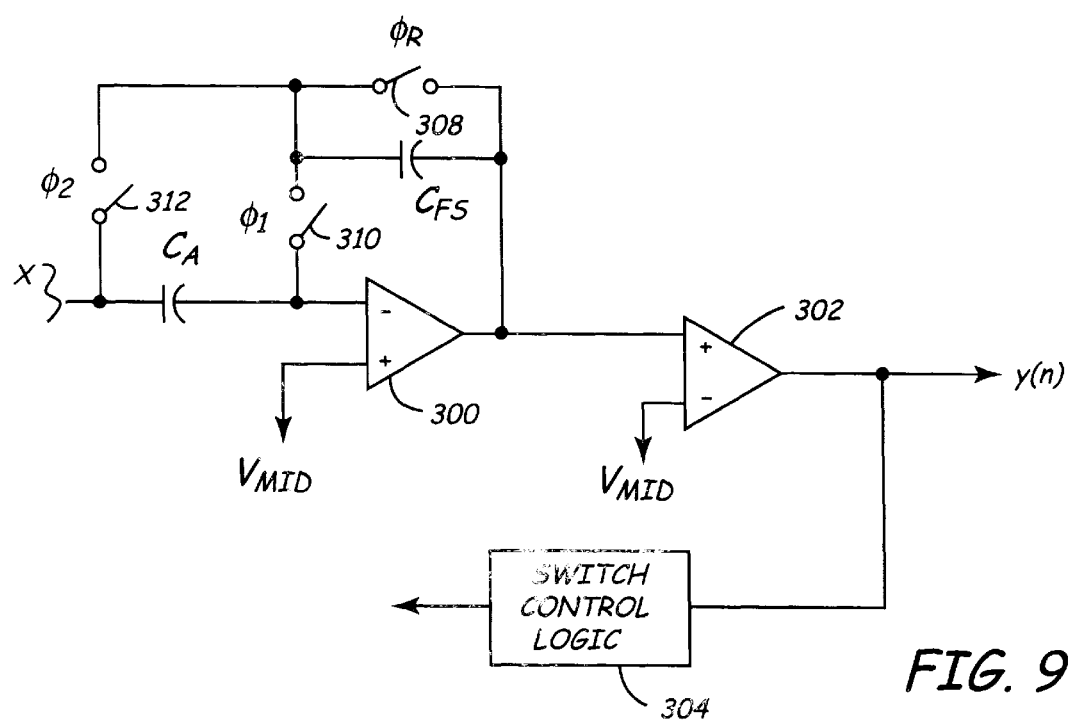
FIG. 9 is a circuit diagram of a second embodiment of a sigma-delta converter useful with the excitation circuit of the present invention.

FIGS. 8 and 9 illustrate two embodiments of a first-order sigma-delta converter useful with the excitation circuits illustrated in FIGS. 4–6. For ease of understanding, a first-order sigma-delta converter is shown and described. Those skilled in the art will recognized that in practice a second-order sigma-delta converter will more likely be employed and that the improvements herein apply to first-order and second-order sigma-delta converters.

As illustrated in FIG. 8, a first-order sigma-delta converter includes a differential amplifier 300 forming an inverting integrator and a comparator 302. The negative input of amplifier 300 is connected directly to node X, the positive input of amplifier 300 is connected to voltage level Vmid, and the output of amplifier 300 is connected to one side of feedback capacitor $C_{FS}$ and to the positive input of comparator 302. The negative input of comparator 302 is connected to voltage level Vmid and the output of comparator 302 provides the output of the circuit, and is connected to switch control logic 304 to provide the control signals to operate the switches of the excitation and sigma-delta converter circuits. Switch 306 couples the input side of feedback capacitor $C_{FS}$ to node X and the negative input of amplifier 300. Switch 308 is connected in parallel with feedback capacitor $C_{FS}$.

In operation of the circuit of FIG. 8, switch 306 is conductive during the second phase $\Phi_2$ to pump the charge at node X (FIGS. 4, 5, or 6) into feedback capacitor $C_{FS}$. Amplifier 300 inverts the charge and produces a voltage output to the second stage of the sigma-delta converter. Comparator 302 provides a signal output y(n) representative of the capacitance ratio $$\frac{(C_H - K_H C_{HR}) - (C_L - K_L C_{LR})}{(C_H - K_H C_{HR}) + (C_L - K_L C_{LR})},$$

and provides synchronizing signals to logic 304.

When it is desired to reset the circuit, switch 308 is made conductive simultaneously with switch 306, thereby discharging feedback capacitor $C_{FS}$.

FIG. 9 illustrates a second embodiment of a first-order sigma-delta converter useful with the excitation circuits of FIGS. 4–6. The circuit of FIG. 9 differs from that of FIG. 8 primarily by the addition of offset capacitor $C_A$. Capacitor $C_A$ is coupled between the negative input of amplifier 300 and node X to compensate for voltage offset of the amplifier. Switch 10 couples capacitor $C_A$ to feedback capacitor $C_{FS}$ during the first phase, $\Phi_1$, thereby charging capacitor $C_A$ with the offset voltage. During the second phase, $\Phi_2$, the charge at node X from the excitation circuit of FIG. 4, 5, or 6 is pumped into feedback capacitor $C_{FS}$ through conducting switch 12.

The excitation circuit of FIGS. 4, 5, or 5 and sigma-delta converter circuit of FIGS. 8 or 9 are embodied on a single circuit board for connection to the sensor capacitors $C_H$, $C_L$, $C_{HR}$ and $C_{LR}$. Moreover, the switches, open lead detectors, amplifiers 108 or 130 of the excitation circuit and at least the digital portion of the sigma-delta converter are preferably embodied as a single chip, thereby conserving power and space.

The present invention overcomes one problem associated with the circuit illustrated in FIG. 2 by employing on-chip amplifiers 104 or 130 having a low input resistance thereby introducing minimal delays due to settling at the high and low values at the outputs of the amplifiers. The reduced settling times of amplifiers 104 and 130 improves accuracy of measurement by the sigma-delta converter at node X, and improves the current requirements during the transition between the high and low values of the amplifier outputs, providing adequate power to operate other maintenance and diagnostic circuits, such as open lead detector 120. Additionally, amplifiers 104 and 130, being on-chip amplifiers, do not require external leads and connection that are a source of leakage and noise. Moreover, sample-and-hold circuits are not required as part of the sigma-delta converter, resulting in reduced power consumption by the transmitter circuit, and increased space availability on the circuit board of the transmitter.

An additional feature of the circuit of FIGS. 4 and 5 is that summing of the charges on the sensing capacitors and the corresponding compensation capacitors occurs during the same phase as the charging of the respective capacitors. This feature tends to cancel noise that might be generated during the two operations. Moreover, since integration in the inverting amplifier occurs during the same phase as charging, noise generated in charging the capacitors is cancelled during integration. FIG. 6 may be modified to accomplish the same result, such as by deleting the connection of switches 145 and 147 to capacitors $C_{HR}$ and $C_{LR}$ and operating switches 144 AND 146 during the respective y and y cycles.

The embodiment of FIG. 6 offers the additional advantage of employing a single amplifier 130 that operates to invert the charge for the compensation capacitors for both sides of the differential sensor. Hence, amplifier 130 inverts the charge from compensation capacitor $C_{HR}$ during one cycle of operation of the circuit, and inverts the charge from compensation capacitor $C_{LR}$ during the second cycle of operation. The dual function of amplifier 130 further reduces power requirements of the transmitter circuit and the space required for the circuit. Since industrial process control transmitters have limited power availability, the reduced power requirement of the excitation circuit permits the availability of power for other purposes.

The present invention thus provides a two-phase excitation circuit for an industrial process control transmitter that charges sensor capacitors and transfers charge representations to the integrator without introducing delays in integrator settling, and without measurement error at high sampling frequencies. The circuit of the present invention eliminates the need for external operational amplifiers that introduced leakage paths and noise sources. The circuit of the present invention eliminates the need for additional sample-and-hold amplifiers as required in prior circuits which require additional power consumption diminish the availability of real estate on the circuit boards in the transmitter.

Although the present invention has been described with reference to preferred embodiments, workers skilled in the art will recognize that changes may be made in form and detail without departing from the spirit and scope of the invention.

What is claimed is:

1. An excitation circuit for charging capacitors of a sensor and for transferring representations of charges on the capacitors to a capacitance-to-digital converter, the sensor having at least one sensing capacitor and at least one compensation capacitor each responding differently to a condition and to error, the excitation circuit including:
    a coupler selectively coupling an excitation source to the sensor to charge the capacitors;
    a first inverting charge amplifier circuit having:
        a first inverting amplifier having an inverting input coupled to the at least one compensation capacitor and having an output,
        a first feedback capacitor coupled between the inverting input and output of the first amplifier, and
        a first auto-zeroing switch selectively coupled in parallel with the first feedback capacitor;
    a first summing node coupled to the output of the first inverting amplifier and to at least one sensing capacitor; and
    a switch logic circuit for selectively operating the coupler.

2. The excitation circuit of claim 1, including a programmable gain control coupled between the output of the first inverting amplifier and the first summing node.

3. The excitation circuit of claim 1, wherein the excitation circuit is on a single circuit board, and the first inverting charge amplifier, first summing node and capacitance-to-digital converter are on a single chip.

4. The excitation circuit of claim 1, wherein the first inverting charge amplifier circuit further includes:
    an offset capacitor coupled to an input of the first inverting amplifier, and
    the coupler couples the first offset capacitor between the first auto-zeroing switch and the excitation source to charge the offset capacitor while coupling the excitation source to the at least one compensation capacitor.

5. The excitation circuit of claim 1, wherein the sensor includes first and second sensing capacitors and first and second compensation capacitors, and the coupler comprises:
    a first switch circuit selectively coupling the excitation source to the sensor to charge the first sensing capacitor and the first compensation capacitor, and
    a second switch circuit selectively coupling the excitation source to the sensor to charge the second sensing capacitor and second compensation capacitor.

6. The excitation circuit of claim 5, wherein the first summing node is coupled to the output of the first inverting amplifier and to the first sensing capacitor, and the excitation circuit further includes:
    a second inverting charge amplifier circuit having:
        a second inverting amplifier having an inverting input coupled to the second compensation capacitor and having an output,
        a second feedback capacitor coupled between the output and the inverting input of the second inverting amplifier, and
        a second auto-zeroing switch selectively coupled in parallel with the second feedback capacitor;
    a second summing node coupled to the output of the second inverting amplifier and the second sensing capacitor;
    an output node; and
    the coupler includes a third switch circuit selectively coupling the first and second summing nodes to the output node,
the switch logic circuit operating the first, second and third switch circuits to charge the first sensing capacitor and first compensation capacitor and to charge the second sensing capacitor and second compensation capacitor during respective first phases, and to couple the first and second summing nodes to the output node during respective second phases.

7. The excitation circuit of claim 6, wherein the second phase has a longer time duration than the first a phase.

8. The excitation circuit of claim 6, wherein the first and second inverting charge amplifier circuits each further includes an offset capacitor coupled between the respective compensation capacitor and the inverting input of the respective inverting amplifier for compensating for voltage offset of the respective inverting amplifier, the respective auto-zeroing switch coupling the respective offset capacitor to the output of the respective inverting amplifier while the respective first and second switch circuits couples the excitation source to the respective compensation capacitor.

9. The excitation circuit of claim 8, including
    a fourth switch circuit coupling the respective offset capacitor between the respective auto-zeroing switch and the excitation source.

10. The excitation circuit of claim 5, wherein the coupler further includes:
    a third switch circuit selectively coupling the first and second compensation capacitors to the inverting input of the first inverting amplifier, selectively coupling the first and second sensing capacitors to the first summing node and selectively coupling the output of the inverting amplifier to the first summing node, the switch logic circuit operating the first, second and third switch circuits to charge the first sensing capacitor and first compensation capacitor and to charge the second sensing capacitor and second compensation capacitor during respective first phases, and to couple the first compensation capacitor to the inverting input of the inverting amplifier and couple the output of the inverting amplifier and the first sensing capacitor to the first summing node and to couple the second compensation capacitor to the inverting input of the inverting amplifier and couple the output of the inverting amplifier and the second sensing capacitor to the first summing node during respective second phases.

11. The excitation circuit of claim 10, wherein the first inverting charge amplifier circuit includes an offset capacitor coupled between the third switch circuit and the inverting input of the inverting amplifier for compensating for voltage offset of the inverting amplifier, the auto-zeroing switch coupling the offset capacitor to the output of the inverting amplifier while the respective first and second switch circuits couples the excitation source to the respective compensation capacitor.

12. The excitation circuit of claim 11, including
a fourth switch circuit coupling the offset capacitor between the respective auto-zeroing switch and the excitation source.

13. The excitation circuit of claim 1, including a transmitter output circuit coupled to receive a digital output from the capacitance-to-digital converter to generate a standardized transmitter output adapted for coupling to a remote receiver.

14. The excitation circuit of claim 13, wherein the standardized transmitter output is selected from the group comprising 4–20 mA, FieldBus and fiber optic.

15. The excitation circuit of claim 1, further including an open lead detection circuit coupled to the output of the first inverting charge amplifier.

16. The excitation circuit of claim 1, wherein the sensor includes first and second sensing capacitors and first and second compensation capacitors, and the excitation source supply supplies at least first, second and third excitation voltage levels, the third excitation voltage level being intermediate the first and second excitation voltage levels, and the coupler comprises:
a first switch circuit selectively coupling the first and second excitation voltage levels to an input side of each of the first and second sensing capacitors and the first and second compensation capacitors,
a second switch circuit selectively coupling the third excitation voltage level to an output side of the first and second sensing capacitors and the first and second compensation capacitors, and
a third switch circuit selectively coupling the output sides of the first and second sensing capacitors to the first summing node and selectively coupling the output sides of the first and second compensation capacitors to the inverting input of the first inverting charge amplifier and selectively coupling the output of the first inverting charge amplifier to the first summing node;

the first inverting charge amplifier having a non-inverting input coupled to the third voltage level, and the switch control logic operates
the first and second switch circuits during a respective first phase to charge the first sensing capacitor and first compensation capacitor,
the third switch circuit during a respective second phase to couple the output of the first sensing capacitor to the first summing node and to couple the output of the first compensation circuit through the first inverting charge amplifier to the first summing node,
the first and second switch circuits during a respective first phase to charge the second sensing capacitor and second compensation capacitor, and
the third switch circuit during a respective second phase to couple the output of the second sensing capacitor to the first summing node and to couple the output of the second compensation circuit through the first inverting charge amplifier to the first summing node, the respective first and second phases being mutually exclusive.

17. The excitation circuit of claim 16, wherein the second phase has a longer time duration than the first phase.

18. An industrial process control transmitter for transmitting an output representative of a process condition comprising:
a sensor having at least one sensing capacitor and at least one compensation capacitor each responding differently to the process condition and to error;
a capacitance-to-digital converter for providing a digital output based on an analog signal;
a transmitter output circuit responsive to the digital output to generate a standardized transmitter output adapted for coupling to a remote receiver; and
an excitation circuit for charging the sensing and compensation capacitors and for transferring an analog signal representative of the process condition to the capacitance-to-digital converter, the excitation circuit including:
a coupler selectively coupling an excitation source to the sensor to charge the capacitors;
a first inverting charge amplifier circuit having:
a first inverting amplifier having an inverting input coupled to the at least one compensation capacitor and having an output,
a first feedback capacitor coupled between the inverting input and output of the first amplifier, and
a first auto-zeroing switch selectively coupled in parallel with the first feedback capacitor;
a first summing node coupled to the output of the first inverting amplifier and to at least one sensing capacitor; and
a switch logic circuit for selectively operating the coupler.

19. The industrial process control transmitter of claim 18, wherein the sensor includes first and second sensing capacitors and first and second compensation capacitors, and the first summing node is coupled to the output of the first inverting amplifier and to the first sensing capacitor, the excitation circuit further includes:
a second inverting charge amplifier circuit having:
a second inverting amplifier having an inverting input coupled to the second compensation capacitor and having an output,
a second feedback capacitor coupled between the output and the inverting input of the second inverting amplifier, and
a second auto-zeroing switch selectively coupled in parallel with the second feedback capacitor;
a second summing node coupled to the output of the second inverting amplifier and the second sensing capacitor;

an output node; and the coupler includes
- a first switch circuit selectively coupling the excitation source to the sensor to charge the first sensing capacitor and the first compensation capacitor,
- a second switch selectively coupling the excitation source to the sensor to charge the second sensing capacitor and the second compensation capacitor, and
- a third switch circuit selectively coupling the first and second summing nodes to the output node, the switch logic circuit operating the first, second and third switch circuits to charge the first sensing capacitor and first compensation capacitor during a first phase and to charge the second sensing capacitor and second compensation capacitor during respective first phases, and to couple the first and second summing node to the output node during respective second phases.

20. The industrial process control transmitter of claim 18, wherein the sensor includes first and second sensing capacitors and first and second compensation capacitors, the coupler includes
- a first switch circuit selectively coupling the excitation source to the sensor to charge the first sensing capacitor and the first compensation capacitor,
- a second switch selectively coupling the excitation source to the sensor to charge the second sensing capacitor and the second compensation capacitor, and
- a third switch circuit selectively coupling the first and second compensation capacitors to the inverting input of the first inverting amplifier, selectively coupling the first and second sensing capacitors to the first summing node and selectively coupling the output of the inverting amplifier to the summing node, the switch logic circuit operating the first, second and third switch circuits to charge the first sensing capacitor and first compensation capacitor and to charge the second sensing capacitor and second compensation capacitor during respective first phases, and to couple the first compensation capacitor to the inverting input of the inverting amplifier and couple the output of the inverting amplifier and the first sensing capacitor to the first summing node and to couple the second compensation capacitor to the inverting input of the inverting amplifier and couple the output of the inverting amplifier and the second sensing capacitor to the first summing node during respective second phases.

* * * * *